US006623926B1

(12) United States Patent
Lohse et al.

(10) Patent No.: US 6,623,926 B1
(45) Date of Patent: Sep. 23, 2003

(54) METHODS FOR PRODUCING 5'-NUCLEIC ACID-PROTEIN CONJUGATES

(75) Inventors: Peter Lohse, Weston, MA (US); Martin C. Wright, Cambridge, MA (US); Michael McPherson, Johnston, RI (US)

(73) Assignee: Phylos, Inc., Lexington, MS (US)

( * ) Notice: Subject to any disclaimer, the term of this patent is extended or adjusted under 35 U.S.C. 154(b) by 149 days.

(21) Appl. No.: 09/585,207

(22) Filed: Jun. 1, 2000

Related U.S. Application Data
(60) Provisional application No. 60/137,032, filed on Jun. 1, 1999, now abandoned.

(51) Int. Cl.[7] ............... C12Q 1/68; A61K 38/03; A61K 38/16
(52) U.S. Cl. ............... 435/6; 435/320.1; 435/91.1; 435/69.7; 536/23.1; 424/179.1; 530/395; 530/391.9; 530/391.5; 514/2
(58) Field of Search ............... 530/395, 391.9, 530/391.5; 435/6, 320.1, 91.1, 69.7; 536/23.1; 424/179.1; 514/2

(56) References Cited

U.S. PATENT DOCUMENTS

| | | | |
|---|---|---|---|
| 4,587,044 | A | 5/1986 | Miller et al. |
| 5,270,163 | A | 12/1993 | Gold |
| 5,541,061 | A | 7/1996 | Fodor et al. |
| 5,547,839 | A | 8/1996 | Dower et al. |
| 5,627,024 | A | 5/1997 | Maruyama et al. |
| 5,643,768 | A | 7/1997 | Kawasaki |
| 5,658,754 | A | 8/1997 | Kawasaki |
| 5,789,208 | A | 8/1998 | Sharon |
| 5,800,992 | A | 9/1998 | Fodor et al. |
| 5,843,701 | A | 12/1998 | Gold et al. |
| 5,849,878 | A | 12/1998 | Cantor et al. |
| 5,965,133 | A | 10/1999 | Cantor et al. |
| 5,985,575 | A | 11/1999 | Wickens et al. |

FOREIGN PATENT DOCUMENTS

| | | |
|---|---|---|
| DE | 19646372 | 11/1996 |
| WO | WO 91/05058 | 4/1991 |
| WO | WO 92/02536 | 2/1992 |
| WO | WO 93/03172 | 2/1993 |
| WO | WO 98/16636 | 4/1998 |
| WO | WO 98/31700 | 7/1998 |
| WO | WO 98/37186 | 8/1998 |
| WO | WO 00/32823 | 6/2000 |
| WO | WO 00/47775 | 8/2000 |

OTHER PUBLICATIONS

Arar et al., "Synthesis and Antiviral Activity of Peptide–Oligonucleotide Conjugates Prepared by Using Nα–(Bromoacetyl)Peptides," *Bioconjugate Chem.* 6:573–577 (1995).

Baskerville et al., "A Ribozyme that Joins Itself to a Peptide," Abstract, RNA '98 Meeting, Madison, WI, May 26–31, 1998.

Bayard et al., "Activation of Ribonuclease L by $(2'-5')(A)_4$–Poly (L–lysine) Conjugates in Intact Cells," *Biochemistry* 25:3730–3736 (1986).

Brenner and Lerner, "Encoded Combinatorial Chemistry," *Proc. Natl. Acad. Sci. USA* 89:5381–5383 (1992).

Cremer et al., "Cocalent Attachment of Ribonucleic Acids to Protein," *J. Prot. Chem.* 11(5):553–560 (1992).

Ghosh et al., "Synthesis of 5'–Oligonucleotide Hydrazide Derivatives and Their Use in Preparation of Enzyme–Nucleic Acid Hybridization Probes," *Analytical BioChemistry* 178:43–51 (1989).

Hanes and Plückthun, "*In vitro* Selection and Evolution of Functional Proteins by Using Ribosome Display," *Proc. Natl. Acad. Sci. USA* 94:4937–4942 (1997).

Haralambidis et al., "The Preparation of Polyamide–Oligonucleotide Probes Containing Multiple Non–Radioactive Labels," *Nucleic Acids Res.* 18:501–505 (1990).

He and Taussig, "Anitbody–Ribosome–mRNA (ARM) Complexes as Efficient Selection Particles for *in vitro* Display and Evolution of Antibody Combining Sites," *Nucleic Acids Research* 25:5132–5134 (1997).

Juby et al., "Facile Preparation of 3' Oligonucleotide–Peptide Conjugates," *Tetrahedron Lett.* 32:879–882 (1991).

Lemaitre et al., "Specific Antiviral Activity of a Poly(L–lysine)–Conjugated Oligodeoxyribonucleotide Sequence Complementary to Vesicular Stomatitis Virus N Protein mRNA Intiation Site," *Proc. Natl. Acad. Sci. USA* 84:648–652 (1987).

Leonetti et al., "Biological Acitvity of Oligonucleotide–Poly(L–lysine) Conjugate: Mechanism of Cell Uptake," *Bioconjugate Chem.* 1:149–153 (1990).

McPherson et al., "Synthesis of an RNA–Peptide Conjugate by Orthongonal Ligation" *SYNLETT* S1:978–980, 1999.

Nielsen et al., "Synthetic Methods for the Implementation of Encoded Combinatorial Chemistry," *J. Am. Chem. Soc.* 115:9812–9813 (1993).

(List continued on next page.)

*Primary Examiner*—Christopher S. F. Low
*Assistant Examiner*—Chih-Min Kam
(74) *Attorney, Agent, or Firm*—Clark & Elbing LLP

(57) ABSTRACT

Disclosed herein is a method for generating a 5'-nucleic acid-protein conjugate, the method involving: (a) providing a nucleic acid which carries a reactive group at its 5' end; (b) providing a non-derivatized protein; and (c) contacting the nucleic acid and the protein under conditions which allow the reactive group to react with the N-terminus of the protein, thereby forming a 5'-nucleic acid-protein conjugate. Also disclosed herein are 5'-nucleic acid-protein conjugates and methods for their use.

26 Claims, 6 Drawing Sheets

OTHER PUBLICATIONS

Niemeyer et al., "Oligonucleotide–Directed Self–Assembly of Proteins: Semisynthetic DNA—Streptavidin Hybrid Molecules as Connectors for the Generation of Macroscopic Arrays and the Construction of Supermolecular Bioconjugates," *Nucleic Acids Research* 22:5530–5539 (1994).

Pieles and Englisch, "Psoralen Convalently Linked to Oligodeoxyribonucleotides: Synthesis, Sequence Specific Recognition of DNA and Photo–Cross–Linking to Pyrimidine Residues of DNA," *Nucleic Acids Research* 17:285–299 (1989).

Proudnikev et al., "Chemical Methods of DNA and RNA Fluorescent Labeling," *Nucleic Acids Research* 24:4535–4542 (1996).

Roberts and Szostak, "RNA–Peptide Fusions for the *in vitro* Selection of Peptides and Proteins," *Proc. Natl. Acad. Sci. USA* 94:12297–12302 (1997).

Salas, "Protein–Priming of DNA Replication" *Ann. Rev. Biochem.* 60:39–71 (1991).

Soukchareun et al. "Preparation and Characterization of Antisense Oligonucleotide–Peptide Hybrids Containing Viral Fusion Peptides," *Bioconjugate Chem.* 6:43–53 (1995).

Tong et al., "The Synthesis of Oligonucleotide–Polyamide Conjugate Molecules Suitable as PCR Primers," *J. Org. Chem.* 58:2223–2231 (1993).

Trask and Muller, "Stabilization of Type I Topoisomerase—DNA Covalent Complexes by Actinomycin D," *BioChemistry* 85:1417–1421 (1988).

Truffert et al., "Synthesis, Purification and Characterization of Two Peptide–Oligonucleotide Conjugates as Potential Artifical Nucleases," *Tetrahedron* 52:3005–3016 (1996).

Vives & Lebleu, "Selective Coupling of a Hihgly Basic Peptide to an Oligonucleotide" *Tetrahedron Lett.* 38:1183–1186 (1997).

Zhao et al., "Site–Specific Modification of a Single–Chain Antibody Using a Novel Glyoxylyl–Based Labeling Reagent," *BioConjugate Chem.* 10:424–430 (1999).

METHODS FOR PRODUCING 5'-NUCLEIC ACID-PROTEIN CONJUGATES

CROSS REFERENCE TO RELATED APPLICATIONS

The application claims the benefit of the filing date of U.S. Provisional Application, U.S. Ser. No. 60/137,032, filed Jun. 1, 1999, now abandoned.

BACKGROUND OF THE INVENTION

In general, the present invention features methods for the preparation of nucleic acid-protein conjugates.

Nucleic acid-protein conjugates, sometimes referred to as nucleic acid-protein fusions, nucleoproteins or nucleopeptides, are naturally-occurring bioconjugates which play a key role in important biological processes. In one particular example, such conjugates play a central role in the process of nucleoprotein-primed viral replication (Salas, Ann. Rev. Biochem. 60, 39–71 (1991)). Accordingly, nucleoproteins as well as nucleopeptides may serve as powerful tools for the study of biological phenomena, and may also provide a basis for the development of antiviral agents.

In addition, conjugates of peptides and nucleic acids have found use in several other applications, such as non-radioactive labels (Haralambidis et al., Nucleic Acids Res. 18, 501–505 (1990)) and PCR primers (Tong et al., J. Org. Chem. 58, 2223–2231 (1993)), as well as reagents in encoded combinatorial chemistry techniques (Nielsen et al., J.A.C.S. 115, 9812–9813 (1993)). In yet other applications, peptides predicted to have favorable interactions with cell membranes, such as polylysine (Leonetti et al., Bioconjugate Chem. 1, 149–153 (1990)), other highly basic peptides (Vives & Lebleu, Tetrahedron Lett. 328, 1183–1186 (1997)), hydrophobic peptides (Juby et al., Tetrahedron Lett. 32, 879–882 (1991)), viral fusion peptides (Soukchareun et al., Bioconjugate Chem. 6, 43–53 (1995)) and peptide signal sequences (Arar et al., Bioconjugate Chem. 6, 573–577 (1995)), have been coupled to oligonucleotides to enhance cellular uptake. Peptides able to chelate metals have also been appended to oligonucleotides to generate specific nucleic acid cleaving reagents (Truffert et al., Tetrahedron 52, 3005–3016 (1996)). And peptides linked to the 3'-end of oligonucleotides have been reported to provide important resistance to 3'-exonucleases (Juby et al., Tetrahedron Lett. 32, 879–882 (1991)).

One particular type of nucleic acid-protein conjugate, referred to as an 10. RNA-protein fusion (Szostak and, Roberts, U.S. Ser. No. 09/007,005; and Roberts'and Szostak, Proc. Natl. Acad. Sci. USA 94, 12297–12302 (1997)), has been used in methods for isolating proteins with desired properties from pools of proteins. To create such, fusions, an RNA and the peptide or protein that it encodes are joined during in vitro translation using synthetic RNA that carries a peptidyl acceptor, such as puromycin, at its 3'-end. In this process, the synthetic RNA, which is devoid of stop codons, is typically synthesized by in vitro transcription from a DNA template followed by 3'-ligation to a DNA linker carrying puromycin. The DNA template sequence causes the ribosome to pause at the 3'-end of the open reading frame, providing additional time for the puromycin to accept the nascent peptide chain and resulting in the production of the RNA-protein fusion molecule.

SUMMARY OF THE INVENTION

The present invention features chemical ligation methods for producing nucleic acid-protein conjugates in good yields. Two different approaches are described. In the first, fusions are formed by a reaction between an unprotected protein carrying an N-terminal cysteine and a nucleic acid carrying a 1,2-aminothiol reactive group. In the second approach, fusion formation occurs as the result of a bisarsenical-tetracysteine interaction.

Accordingly, in a first aspect, the invention features a method for generating a 5'-nucleic acid-protein conjugate, the method involving: (a) providing a nucleic acid which carries a reactive group at its 5' end; (b) providing a non-derivatized protein; and (c) contacting the nucleic acid and the protein under conditions which allow the reactive group to react with the N-terminus of the protein, thereby forming a 5-nucleic acid-protein conjugate.

In a related aspect, the invention features a 5'-nucleic acid-protein conjugate which includes a nucleic acid bound through its 5'-terminus or a 5'-terminal reactive group to the N-terminus of a non-derivatized protein.

In various preferred embodiments of these aspects, the nucleic acid is greater than about 20 nucleotides in length; the nucleic acid is greater than about 120 nucleotides in length; the nucleic acid is between about 2–1000 nucleotides in length; the protein is greater than about 20 amino acids in length; the protein is greater than about 40 amino acids in length; the protein is between about 2–300 amino acids in length; the contacting step is carried out in a physiological buffer; the contacting step is carried out using a nucleic acid and a protein, both of which are present at a concentration of less than about 1 mM; the nucleic acid is DNA or RNA (for example, mRNA); the nucleic acid includes the coding sequence for the protein; the N-terminus of the non-derivatized protein is a cysteine residue; the N-terminal cysteine is exposed by protein cleavage; the reactive group is an aminothiol reactive group; the protein includes an α-helical tetracysteine motif located proximal to its N-terminus; the α-helical tetracysteine motif includes the sequence cys-cys-X-X-cys-cys SEQ. ID. NO: 6, wherein X is any amino acid; the reactive group is a bisarsenical derivative; the conjugate is immobilized on a solid support (for example, a bead or chip); and the conjugate is one of an array immobilized on a solid support.

In another related aspect, the invention features a method for the selection of a desired nucleic acid or a desired protein, the method involving: (a) providing a population of 5'-nucleic acid-protein conjugates, each including a nucleic acid bound through its 5'-terminus or a 5'-terminal reactive group to the N-terminus of a non-derivatized protein; (b) contacting the population of 5'-nucleic acid-protein conjugates with a binding partner specific for either the nucleic acid or the protein portion of the desired nucleic acid or desired protein under conditions which allow for the formation of a binding partner-candidate conjugate complex; and (c) substantially separating the binding partner-candidate conjugate complex from unbound members of the population, thereby selecting the desired nucleic acid or the desired protein.

In yet another related aspect, the invention features a method for detecting an interaction between a protein and a compound, the method involving: (a) providing a solid support that includes an array of immobilized 5'-nucleic acid-protein conjugates, each conjugate including a nucleic acid bound through its 5'-terminus or a 5'-terminal reactive group to the N-terminus.of a non-derivatized protein; (b) contacting the solid support with a candidate compound under conditions which allow an interaction between the protein portion of the conjugate and the compound; and (c)

analyzing the solid support for the presence of the compound as an indication of an interaction between the protein and the compound.

In various preferred embodiments of these methods, the method further involves repeating steps (b) and (c); the compound is a protein; the compound is a therapeutic; the nucleic acid is greater than about 20 nucleotides in length; the nucleic acid is greater than about 120 nucleotides in length; the nucleic acid is between about 2–1000 nucleotides in length; the protein is greater than about 20 amino acids in length; the protein is greater than about 40 amino acids in length; the protein is between about 2–300 amino acids in length; the nucleic acid is DNA or RNA (for example, mRNA); the nucleic acid includes the coding sequence for the protein, the N-terminus of the non-derivatized protein is a cysteine residue; the reactive group is an aminothiol reactive group; the protein includes an α-helical tetracysteine motif located proximal to its N-terminus; the α-helical tetracysteine motif includes the sequence, cys-cys-X-X-cys-cys SEQ. ID. NO: 6, wherein X is any amino acid; the reactive group is a bisarsenical derivative; the conjugate is immobilized on a solid support (for example, a bead or chip); and the conjugate is one of an array immobilized on a solid support.

As used herein, by a "5'-nucleic acid-protein conjugate" is meant a nucleic acid which is covalently bound to a protein through the nucleic acid's 5' terminus.

By a "nucleic acid" is meant any two or more covalently bonded nucleotides or nucleotide analogs or derivatives. As used herein, this term includes, without limitation, DNA, RNA, and PNA.

By a "protein" is meant any two or more amino acids, or amino acid analogs or derivatives, joined by peptide or peptoid bond(s), regardless of length or post-translational modification. As used herein, this term includes, without limitation, proteins, peptides, and polypeptides.

By "derivatize" is meant adding a non-naturally-occurring chemical functional group to a protein following the protein's translation or chemical synthesis. "Non-derivatized" proteins are not treated in this manner and do not carry such non-naturally-occurring chemical functional groups.

By a "physiological buffer" is meant a solution that mimics the conditions in a cell. Typically, such a buffer is at about pH 7 and may be at a temperature of about 37° C.

By a "solid support" is meant any solid surface including, without limitation, any chip (for example, silica-based, glass, or gold chip), glass slide, membrane, bead, solid particle (for example, agarose, sepharose, or magnetic bead), column (or column material), test tube, or microtiter dish.

By an "array" is meant a fixed pattern of immobilized objects on a solid surface or membrane. As used herein, the array is made up of nucleic acid-protein fusion molecules (for example, RNA-protein fusion molecules). The array preferably includes at least $10^2$, more preferably at least $10^3$, and most preferably at least $10^4$ different fusions, and these fusions are preferably arrayed on a 125×80 mm, and more preferably on a 10×10 mm, surface.

By a "population" is meant more than one molecule.

The present invention provides a number of advantages. For example, although conjugates of between 2–1000 nucleotides and 2–300 amino acids are preferred, nucleic acid-protein conjugates of any desired molecular weight may be generated using the methods of the invention because the nucleic acid as well as the protein may be produced independently using well-known synthetic and biological methods. These post-synthetic ligation methods are therefore advantageous over fully synthetic techniques where stepwise buildup of nucleic acid-peptide conjugates generally allows preparation of only limited size conjugates, typically of less than 20 nucleotides and less than 20 amino acids in length.

In addition the reactions described herein (for example, the reaction between the N-terminal cysteine and the 1,2-aminothiol reactive group on the nucleic acid) are chemoselective over other nucleophilic groups on the protein, thus leading to regiospecific links between proteins and nucleic acids. This contrasts with known methods for the synthesis of protein-nucleic acid conjugates which often rely on reactions between a nucleophilic group on the protein and an electrophile on the nucleic acid moiety (Bayard et al., Biochemistry 25, 3730–3736 (1986); Cremer et al., J. Prot. Chem. 11(5), 553–560 (1992)). In these reactions, multiple nucleophilic side chains on the protein compete for reaction with the electrophile leading to non-specific links between protein and nucleic acid and thus generating a heterogenous mixture of conjugate products.

In yet other advantages, the present ligation reactions work efficiently under mild conditions in physiological buffers. Consequently, protein structure is not disrupted under the ligation conditions used, and conjugates carrying functional proteins can be formed. In addition, the present ligation reactions work efficiently with reactant concentrations in the $\mu$M range. Consequently, dilute preparations of protein and nucleic acid can be used for conjugate preparation.

The present techniques also provide advantages with respect to the conjugates themselves. Most notably, the conjugate nucleic acid (for example, RNA) is linked to the amino-terminus of the conjugate protein. This type of fusion leaves the protein's carboxy-terminus unmodified and is particularly beneficial when the carboxy-terminal amino acids are involved with protein structure or function, or participate in interactions with other species.

In addition, with respect to RNA-protein fusions, efficient ligation in aqueous buffers at low concentrations of reactands allows the fusion of nascent proteins to their encoding RNAs while bound to the ribosome. Pretranslational 3'-modification of the mRNA as described for 3'-fusions (Szostak and Roberts, U.S. Ser. No. 09/007,005; and Roberts and Szostak, Proc. Natl. Acad. Sci. USA 94, 12297–12302 (1997)) is unnecessary, because the 3'-end of the mRNA is not involved in ligation. Moreover, because of the lack of involvement of the 3'-end of the RNA in ligation, the present technique facilitates the production of RNA-protein fusions using RNAs from a variety of sources. In one particular example, RNA (for example, mRNA) libraries with heterogeneous 3'-termini may be readily used for the synthesis of 5'-mRNA-protein fusions. In another example, cellular RNA may be used for fusion formation.

Finally, the present invention provides a quantitative advantage for the production of RNA-protein fusions by simplifying ribosome turnover and thereby optimizing fusion synthesis. In particular, because conjugate proteins are linked through their N-termini to conjugate nucleic acids, the fusion products are released in unhindered fashion from the native ribosome following translation, allowing free ribosomes to undergo further rounds of translation. This multiple turnover allows for the synthesis of larger pools of RNA-protein fusions than is currently available with single turnover at the ribosome (Szostak and Roberts, U.S. Ser. No.

09/007,005; and Roberts and Szostak, Proc. Natl. Acad. Sci. USA 94, 12297–12302 (1997)).

The nucleic acid-protein fusions (for example, the mRNA-protein fusions) of the invention may be used in any selection or in vitro evolution technique. For example, these fusions may be used in methods for the improvement of existing proteins or the evolution of proteins with novel structures or functions, particularly in the areas of therapeutic, diagnostic, and research products. In addition, 5'-RNA-protein fusions find use in the functional genomics field; in particular, these fusions (for example, cellular mRNA-protein fusions) maybe used to detect protein-protein interactions in a variety of formats, including presentation of fusion arrays on solid supports (for example, beads or microchips).

Other features and advantages of the invention will be apparent from the following detailed description, and from the claims.

DETAILED DESCRIPTION

The present methods for the synthesis of nucleic, acid-protein conjugates are based on chemical ligation reactions which take place between the nucleic acid and the protein components.

Figure 1:
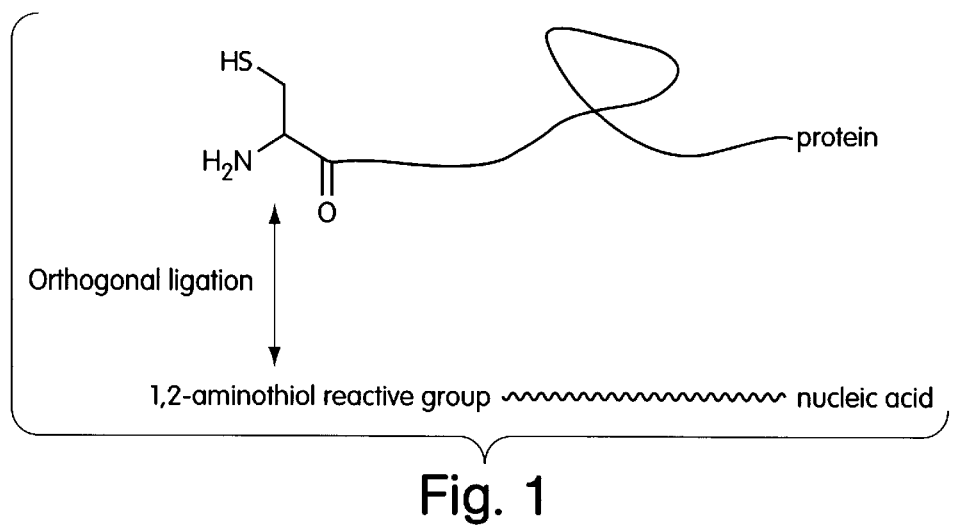
FIG. 1 is a diagram which illustrates the general approach of the invention for generating nucleic acid-protein conjugates.
Figure 2:
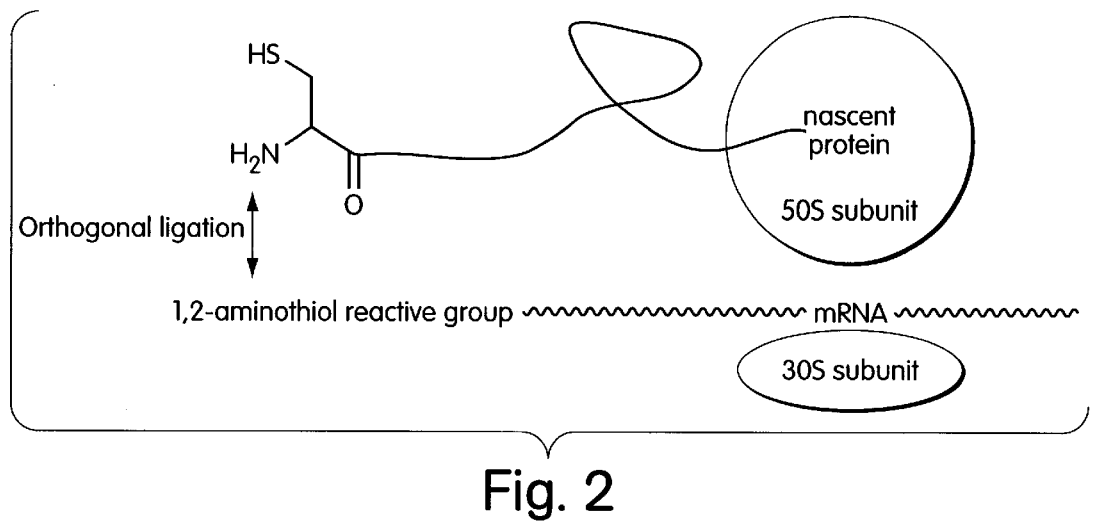
FIG. 2 is a diagram which illustrates the general approach for generating fusions between a protein and its encoding mRNA on the ribosome.

In the first approach, the ligation reaction takes place between an unprotected protein carrying an N-terminal cysteine and a nucleic acid carrying a 1,2-aminothiol reactive group. The ligation reaction is performed generally as described for the synthesis of proteins from protein fragments (see, for example, Brenner, in Peptides, Proceedings of the Eighth European Peptide Symposium, Beyermann, ed. (North-Holland, Amsterdam, 1967), pp. 1–7; Kemp & Carey, J. Org. Chem. 58,2216 (1993); Liu & Tam, J. Am. Chem. Soc. 116,4149 (1994); Dawson et al., Science 266, 776. (1994)). A fast chemoselective reaction followed by intramolecular amide bond formation leads to a covalent link between the nucleic acid and protein. This reaction requires the protein to carry an N-terminal cysteine and the nucleic acid to carry a 1,2-aminothiol reactive group. The general approach is illustrated in FIG. 1. Ligation of a protein to its encoding RNA while bound to the ribosome is illustrated in FIG. 2.

Preparation of Proteins for Orthogonal Ligation

The first ligation scheme according to the invention requires the protein to carry an N-terminal cysteine. Such proteins may be easily prepared synthetically using standard chemical synthetic methods. Alternatively, proteins may be prepared by biological or recombinant methods. These proteins, however, typically do not carry an N-terminal cysteine, instead beginning with an N-terminal methionine residue due to translational initiation at an AUG start codon. Various methods maybe utilized to expose a cysteine at the N-terminus of the conjugate protein. In one particular example, endogenous aminopeptidase activity present in acellular lysate may be used to remove the N-terminal methionine, thereby.exposing the penultimate amino acid at the N-terminus (Moerschell et al., J. Biol. Chem. 265, 19638–19643 (1990)). Alternatively, an N-terminal fragment may be cleaved from each protein in a population of proteins having homogeneous N-termini using a sequence-specific protease. This cleavage reaction produces a population of proteins, each having an N-terminal cysteine (that is, the amino acid C-terminal to the cleavage site). Suitable proteases for this purpose include, without limitation, Factor Xa and Enterokinase (both of which are available from New England Biolabs, Inc., Beverly, MA). These proteases are used in accordance with the manufacturer's instructions.

Preparation of Nucleic Acids for Orthogonal Ligation

The first ligation method of the invention also requires a nucleic acid which carries a 1,2-aminothiol reactive group. This group may be introduced during the synthesis of the nucleic acid or after synthesis (post-synthetically) by means of a 1,2-aminothiol reactive modifier.

Nucleic acids or nucleic acid analogs may be synthesized by standard chemical or enzymatic methods. Heterogenous mixtures of nucleic acids (for example, pools of random sequences or cellular mRNA libraries) may also be readily utilized. Preferably, for fusion formation on a ribosome, the RNA utilized contains no inadvertent stop codons.

For the incorporation of the thiol or thiophosphate group into the nucleic acid, any of a number of standard techniques may be exploited. For example, thiol groups may be incorporated into DNA by chemical means (see thiolmodifiers, Glen Research, Sterling, Virginia; Raines & Gottlieb, RNA 4, 340–345 (1998); Gundlach et al., Tetrahedron Lett. 38, 4039 (1997); Coleman & Siedlecki, J. Am. Chem. Soc. 114, 9229 (1992)). Alternatively, terminal thiophosphate groups may be prepared by chemical phosphorylation followed by oxidation with a sulfurizing reagent (Glen Research, Sterling, Va.). protein conjugates (SEQ ID NO: 5) using a bisarsenical-tetracysteine interaction.

In yet another approach, thiol and thiophosphate groups may be incorporated into RNA by enzymatic means. In one preferred method for the generation of 5'-modified RNA, transcription is carried out in the presence of GMPαS, GDPβS or GTPγS, followed by chemical modification of the 5'-thiophosphate group as described, for example, in.Burgin & Pace, EMBO Journal 9, 4111–4118 (1990); and Logsdon et al., Anal. Biochem. 205, 36–41 (1992). Alternatively, guanosine derivatives carrying the 1,2-aminothiol reactive group may be used to initiate transcription as described, for example, in Martin & Coleman, Biochemistry 28, 2760–2762 (1989); and Logsdon et al., Anal. Biochem. 205, 36–41;(1992). For any of these techniques, GMPAS may be purchased from Amersham, Buckinghamshire, UK, and.GTPγS may be purchased from Fluka, Milwaukee, Wis.

Figure 3:
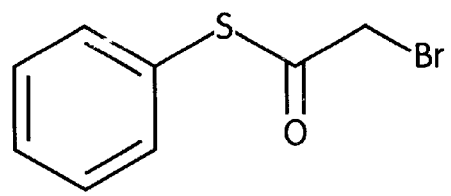
FIG. 3 is a diagram which illustrates the 1,2-aminothiol reactive group modifier, "phenyl-α-bromothioacetate."

A preferred 1,2-aminothiol reactive modifier is phenyl-β-bromothioacetate, shown in FIG. 3. This compound may be synthesized using the procedure of Gennari et al., Tetrahedron 53(16), 5909–5924 (1997)). Specifically, this compound was prepared as follows. To a cooled (0° C.) solution protein conjugates (SEQ ID NO: 5) using a bisarsenical-tetracysteine interaction. protein conjugates (SEQ ID NO: 5) using a bisarsenical-tetracysteine interaction of benzenethiol (0.551 g, 5 mmol, 0.51 ml) in dry dichloromethane (10ml) was added dry pyridine(0.435 g, 5.5 mmol, 0.45 ml). Bromoacetyl chloride (Fluka, 0.787 g, 5 mmol, 0.417 ml) in dry dichloromethane (10 ml) was added dropwise. After stirring at 0° C. for 60 minutes, the reaction was poured into cold water (20 ml). The organic phase was separated and washed with a cold 5% aqueous solution of NaOH, water, dried ($Na_2SO_4$), and the solvent removed in vacuo to leave a yellow-brown oil. Purification by Kugelrohr distillation gave the product as a clear oil (0.88 g, 76%). $^1$H NMR (300 MHz, $CDCl_3$) δ 4.12 (s, 2H, —$CH_2$—), 7.44 (s, 5H, arom). $^{13}$C NMR (100MHz, $CDCl_3$) δ 33.2 (—$CH_2$—), 129.3 (arom), 129.8 (arom), 134.9 (arom), 190.7 (—C=O). MS (PCI, $NH_3$) 232 $[M+H]^+$.

The modifier shown in FIG. 3 has been derived from 1,2-amiothiol reactive groups described for orthogonal ligation of peptide fragments (Dawson et al., Science 266, 776–779 (1994); Liu & Tam Proc. Natl. Acad. Sci. USA 91, 6584–65881(1994)).

Figure 4:
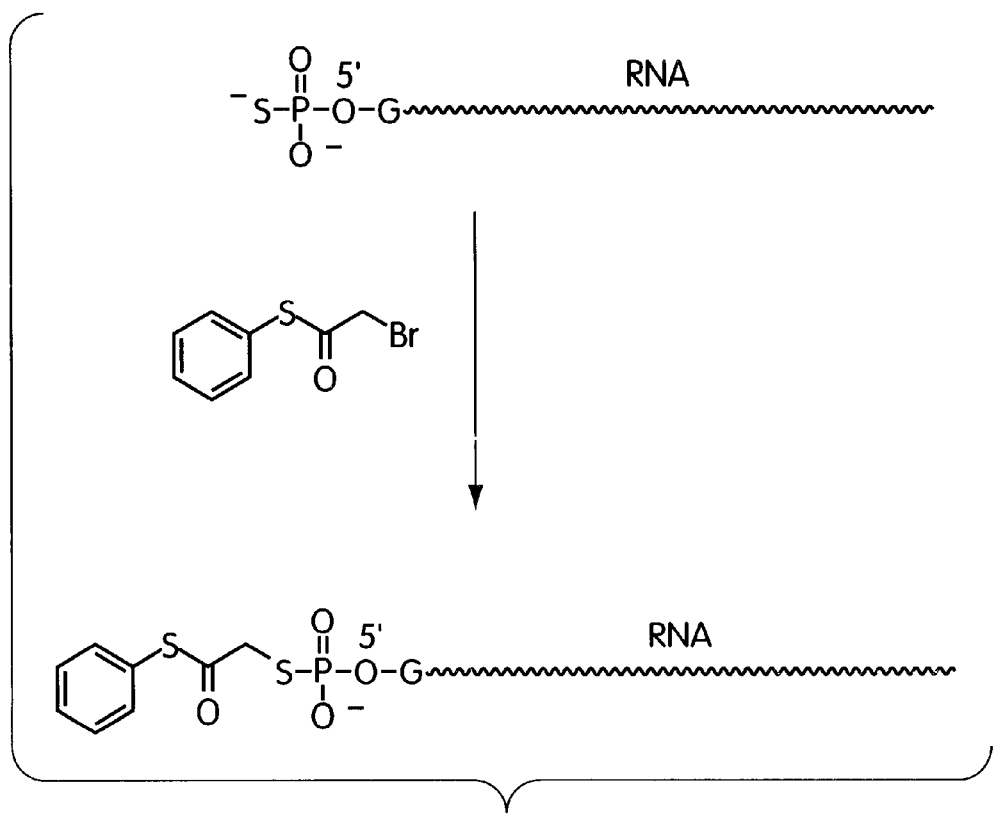
FIG. 4 is a diagram which illustrates alkylation of 5'-GMPS-modified RNA with phenyl-α-bromothioacetate.

Alkylation of 5'-thiophosphate RNA with phenyl-α-bromothioacetate (FIG. 3) is illustrated in FIG. 4. This alkylation step has been carried out as follows. 10 μM GMPS-RNA labeled with $^{32}$P was reacted with 8 mM phenyl-bromothioacetate in 8% DMSO, 82 mM sodium phosphate buffer, pH6.8, at room temperature for 40 minutes. After reaction, the mixture was extracted 4 times with chloroform to remove unreacted bromide. Precipitation was avoided because of the possibility of exchanging the thioester with ethanol.

Conjugate Formation Using Orthogonal Ligation

Figure 5:
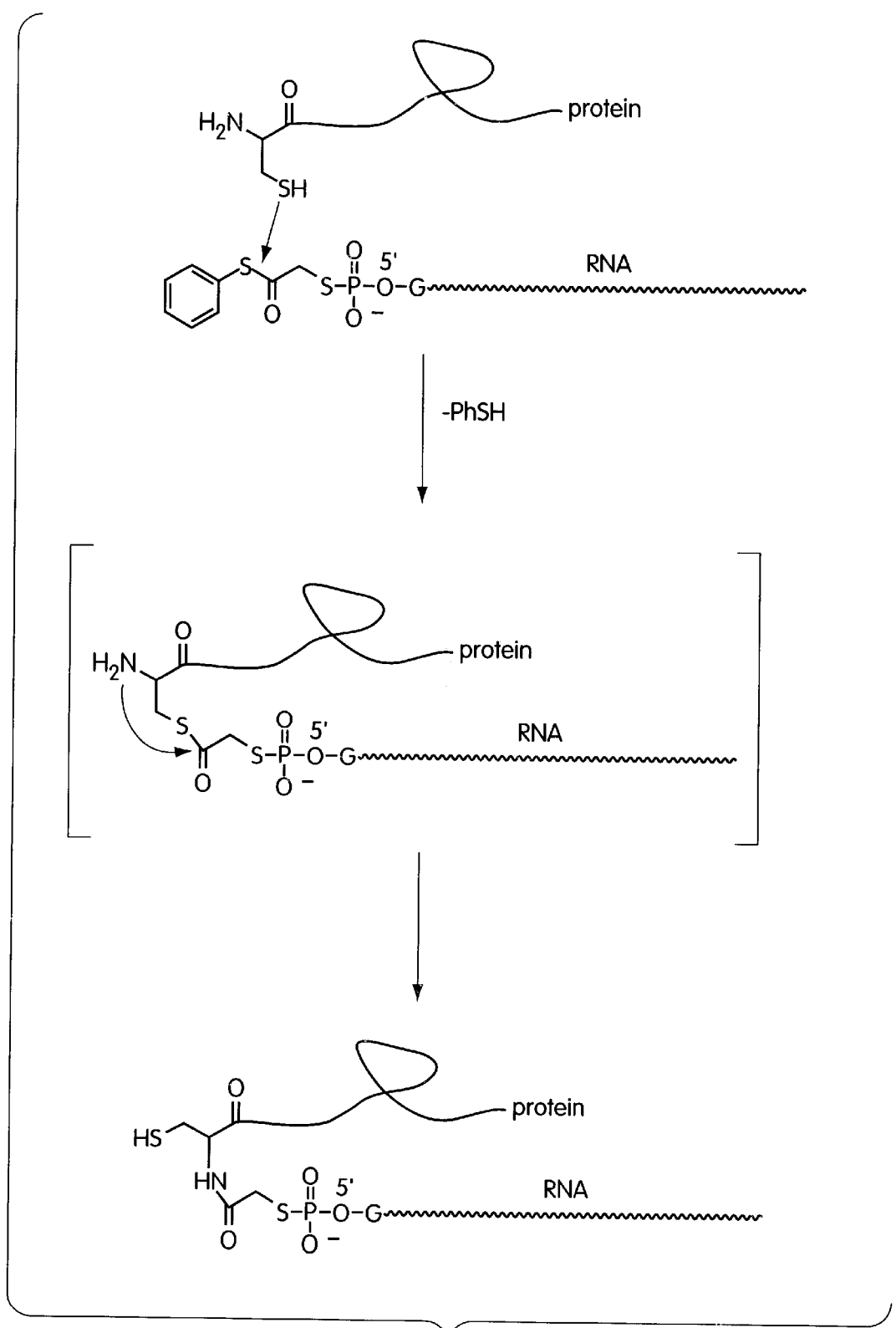
FIG. 5 is a diagram which illustrates an orthogonal ligation reaction between a nucleic acid carrying a thioester functional group and a protein carrying an N-terminal cysteine.

Orthogonal ligation of protein and nucleic acid according to this first method is based on a fast chemoselective thiol-exchange followed by intramolecular amide bond formation, leading to a covalent link between a nucleic acid and a protein. This method, which is illustrated diagrammatically in FIG. 5, allows efficient ligation of RNA and peptide at μM concentrations of reactands. When this, reaction has been carried out, no side products have been detected.

In one particular ligation reaction, 2.5 μM thioester RNA of the following sequence (SEQ ID NO: 1):
thiophosphate-GGG-N80-CCGUGAAGAGCAUUGG was reacted with 25 μM peptide 1 (CSKGFGFVSFSYK-biotin; SEQ ID NO: 2), 25 μM peptide 2 (CRKKRRQRRRPPQGSQTHQVSLSKQK-biotin; SEQ ID NO: 3), or 25 μM peptide 3 (MSKGFGFVSFSYK-biotin; SEQ ID NO: 4) in 80 mM sodium phosphate buffer pH6.8 and 0.5% thiophenol for 2 hours at 30° C. After reaction, the RNA was purified on a polyacrylamide gel and then bound to neutravidin-agarose (Pierce). Bound RNA was eluted with 10 μg/ml proteinase K for 5 minutes. Scintillation counting revealed that 10–12% of the RNA was linked to biotinylated peptides 1 and 2 carrying an N-terminal cysteine, whereas peptide 3 reacted with less than 0.2% of the RNA.

In a further experiment, 1 μM thioester-RNA was reacted with 1 mM peptide 2 under the conditions described above, for 3 hours or 20 hours. The reactions were analyzed by electrophoresis using a 6% polyacrylamide TBE/urea gel (Novex). Under these conditions, 50% of the RNA had reacted in less than 3 hours, but no additional reaction was observed following a prolonged incubation.

Orthogonal ligation may also be used to ligate RNA and protein while these complexes are bound to the ribosome, either during or after translation (see FIG. 2), thereby generating 5'-fusions between an mRNA and its encoded peptide in a pseudo-intermolecular reaction. In one preferred method, the mRNA is used in a cell-free translation system and shows the following properties: (1) the mRNA carries a 1,2-aminothiol reactive group at its 5'-end; (2) the mRNA encodes an N-terminal protease recognition sequence followed by the amino acid cysteine; (3) the mRNA.codes for a protein which is at least 40–50 amino acids long; and (4) the mRNA is devoid of stop codons.

The defined minimal protein length of 40–50 amino acids ensures that the N-terminus of a nascent protein extends to the surface of the ribosome, thus exposing the recognition sequence to protease cleavage. The absence of stop codons prevents release of the mRNA from the ribosome. Addition of Mg salt and washing buffer at low temperature stalls and stabilizes the mRNA-ribosome-protein complex after translation (Hanes & Plueckthun, Proc. Natl. Acad. Sci. USA 94, 4937–4942 (1997)). Protease treatment maybe carried out in this same buffer to expose the N-terminal cysteine on the nascent, ribosome-bound protein. Subsequently, orthogonal ligation between the 5'-terminal 1,2-aminothiol reactive group and the N-terminal cysteine can take place, leading to fusions between nascent proteins and their encoding mRNAs.

To further enhance the ability to efficiently form fusions on the ribosome, stalled mRNA-ribosome-protein complexes (prepared, for example, by the method of Hanes & Plueckthun, Proc. Natl. Acad. Sci. USA 94, 4937–4942 (1997)) may be prepared from cell-free translation systems in which the concentration of cysteine is reduced. Preparation of lysates which are devoid or which contain only a minimal amount of cysteine (preferably, <1 μM) have been described (see, for example, the instruction manual on in vitro translation kits, Ambion, Tex.). A low concentration of competing free cysteine in the lysate may increase the efficiency of productive orthogonal ligation reactions between the N-terminal cysteine of an encoded protein and the 5'-terminal 1,2 aminothidl reactive group, thus increasing RNA-protein fusion yields.

Bisarsenical-Tetracysteine Conjugate Formation

An alternative method for the conjugation of nucleic acids and proteins is through a bisarsenical-tetracysteine interaction. This method of conjugate formation relies on the affinity of organic arsenicals for sulfhydryl-containing compounds (Webb, in Webb (ed.), Enzyme and Metabolic Inhibitors, vol. 3, Academic Press, New York 1966, Cullen et al., J. Inorg. Biochem 21, 179 (1984)), an interaction which has been utilized successfully in the in vivo, sequence-specific identification of fusion proteins which carry non-native sequences consisting of tetracysteine motifs within μ-helical structures (Griffin et al., Science 281, 269–272 (1998)). The technique is shown schematically in FIG. 6.

Figure 6:
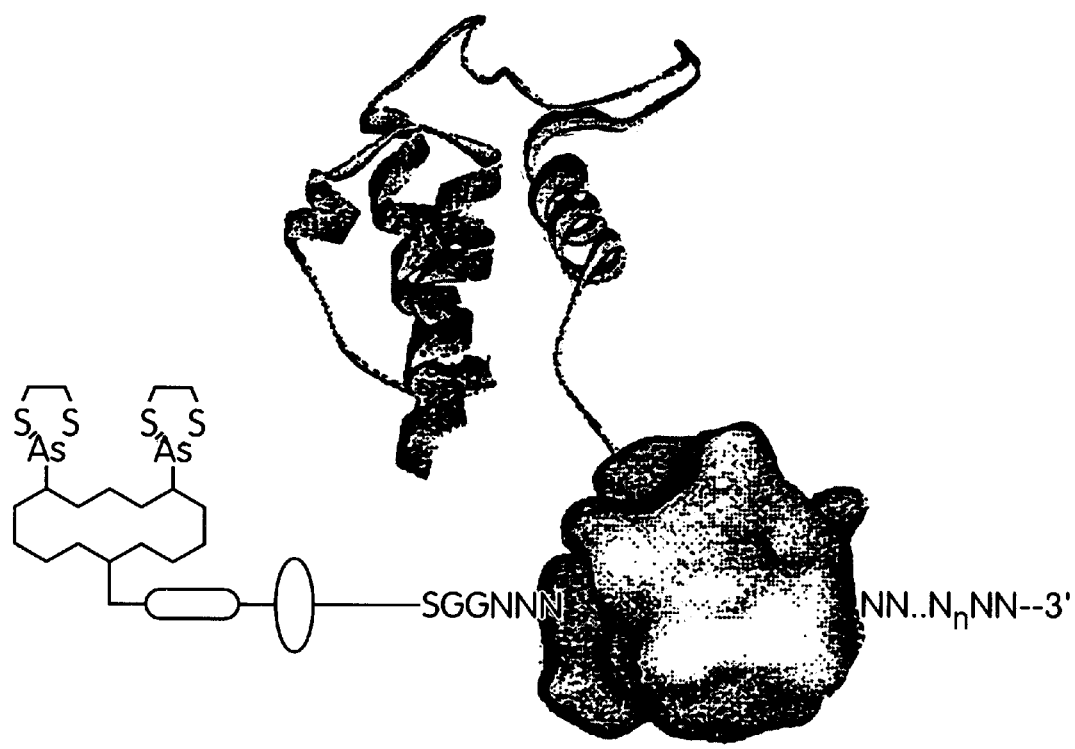
FIG. 6 is a diagram which illustrates the formation of nucleic acid-protein conjugates (SEQ ID NO: 5) using a bisarsenical-tetracysteine interaction.

As shown in FIG. 6, the 5'-terminus of the mRNA is modified with a bisarsenical derivative which is capable of binding an μ-helical tetracysteine motif. The modified message encodes an amino acid sequence which is chosen for, or designed to have a propensity to form α-helices under physiological conditions. Such a modified message may contain a nucleic acid sequence that encodes an amino acid sequence chosen for its propensity to form α-helices under .conditions compatible with in vitro translation. A tetracysteine motif of the form CysCysXXCysCys SEQ. ID. NO: 6 is included within, the helix to create the necessary geometry for thiol exchange. The cys4 α-helix is formed preferably at the N-terminus of the encoded protein. This motif may either be introduced through mutation of an existing (α-helix within the native protein (for example, by the approach of Griffin et al., Science 281, 269–2.72 (1998))or by fusion of the motif to the N-terminus of the protein of interest (for example, during chemical protein synthesis). A tetracysteine motif of the form, cys, cys+1, cys+4, cys+5 is included within the helix to create the necessary geometry for bisarsenical chelation. A tricyclic scaffold is used to allow sufficient spatial orientation of the dithiarsolane moieties to bind the tetracysteine motif effectively. The bisarsenical derivative features a reactive moiety for the regiospecific attachment of the compound to the nucleic acid terminus. This attachment functionality may also be used for derivatization of the bisarsenical compound to a solid phase.

Figure 7:
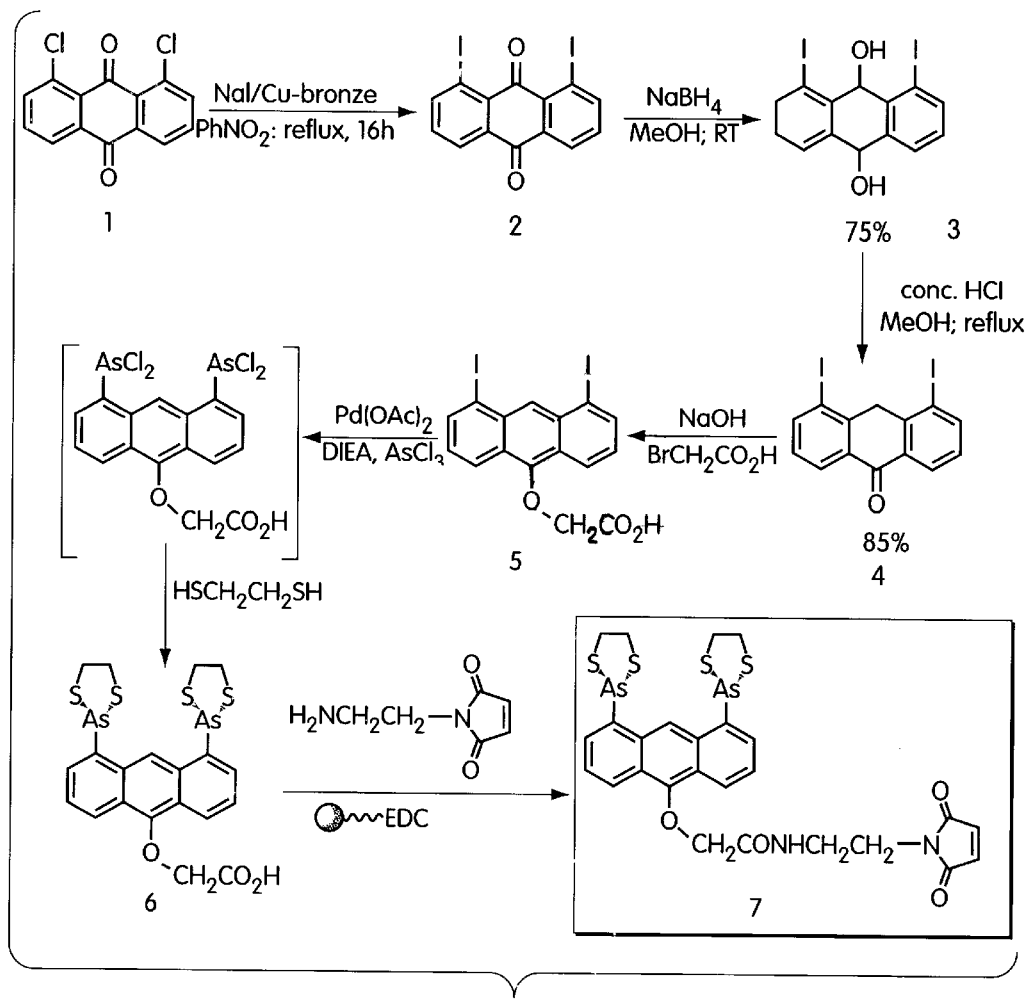
FIG. 7 is a diagram which illustrates an exemplary synthetic scheme for the synthesis of a bisarsenical derivative.

One exemplary scheme for the synthesis of a bisarsenical derivative which encompasses the above features is outlined in FIG. 7. The tricyclic scaffold, 4,5-diiodo-9(10H)-anthracenone 4 is constructed from 1,8-dicholoranthraquinone 1 using standard methods (as described, for example, in Lovell & Joule, Synth. Commun. 27(7), 1209–1215 (1997)). The anthracenone nucleus serves as a handle to introduce a linker via O-alkylation to form compound 5, as described, for example, in Johnstone and Rose (Tetrahedron 35, 2169–2173 (1979)) or Loupy et al. (Bull. Soc. Chim. Fr. 1027–1035 (1987)). Dithiarsolane formation may be achieved by transmetallation via transition metal-mediated catalysis (as described, for example, in Griffin et al., Science 281, 269–272 (1998)) with concomitant reaction with the appropriate dithiol. Introduction of the attachment moiety via carboxylic acid-activated amide formation completes the synthesis of 7. This step may be carried out as described, for example, in Desai and Stramiello, Tet. Letts. 34 (48), 7685–7688 (1993).

Figure 8:
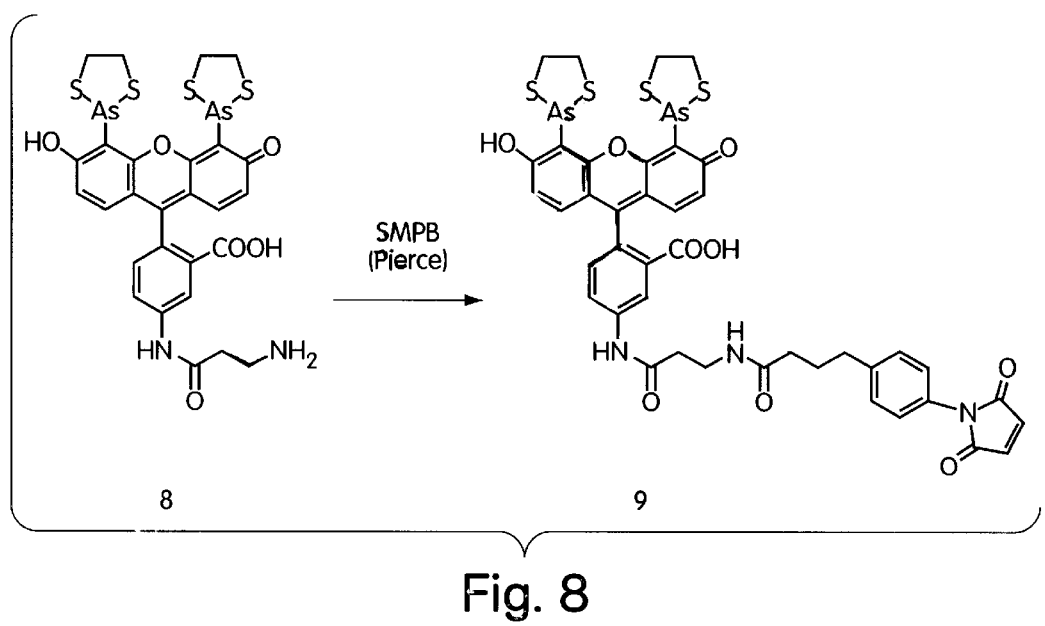
FIG. 8 is a diagram which illustrates a second exemplary synthetic scheme for the synthesis of a bisarsenical derivative.

Another scheme for preparing an amino-tethered bisarsenical fluorescein derivatives is described by Thorn et al., Protein Science 9: 213–217. (2000). Reaction with succinimidyl 4-(p-maleimidophenyl butyrate (SMPB, Pierce, Rockford, Ill.) yields a maleic imid-tethered derivative of bisarsenical fluorescein (as shown in FIG. 8).

These tethered derivatives (compound 7 in FIG. 7) and (compound 9 in FIG. 8) may be attached to the 5' end of a 5' thiol RNA, for example, by the method of Hermanson, Biocbnjugate Techniques, Academic Press, San Diego Calif. (1996); and Goodchild in Meares (ed.), Perspectives in Bioconjugate Chemistry, American Chemical Society, Washington, D.C. 1993. This putative cys4-helix binding molecule may also mediate the formation of nucleic-acid protein, conjugates through attachment at the 3'-termninus of the nucleic acid (Cremer et al., J. Protein Chem. 11(5), 553–560 (1992). The conjugation reaction between the nucleic acid carrying the bisarsenical derivative and the protein may be carried out in buffer or lysate.

Other embodiments are within the claims.

What is claimed is:

1. A method for generating a 5'-nucleic acid-protein conjugate, said method comprising contacting a non-derivatized protein and a nucleic acid which carries a reactive group at its 5' end under conditions that allow said reactive group to react with an N-terminus of said non-derivatized protein, thereby forming a 5'-nucleic acid-protein conjugate, wherein said non-derivatized protein comprises an N-terminal cysteine and the nucleic acid reactive group is an aminothiol reacting group, or wherein said non-derivatized protein comprises an α-helical tetracysteine motif located proximal to the N-terminus and the nucleic acid reactive group is a bisarsenical group that is reactive with the tetracysteine group.

2. The method of claim 1, wherein said nucleic acid is about 20 nucleotides or greater in length.

3. The method of claim 2, wherein said nucleic acid is about 120 nucleotides or greater in length.

4. The method of claim 1, wherein said nucleic acid is greater than 120 nucleotides in length.

5. The method of claim 1, wherein said protein is about 20 amino acids or greater in length.

6. The method of claim 5, wherein said protein is about 40 amino acids or greater in length.

7. The method of claim 1, wherein said protein is between 2–300 amino acids in length.

8. The method of claim 1, wherein said contacting step is carried out in a physiological buffer.

9. The method of claim 1, wherein said contacting step is carried out using a nucleic acid and a protein, both of which are present at a concentration of less than 1 mM.

10. The method of claim 1, wherein said nucleic acid is DNA.

11. The method of claim 1, wherein said nucleic acid is RNA.

12. The method of claim 11, wherein said RNA is mRNA.

13. The method of claim 1, wherein said nucleic acid comprises the coding sequence for said protein.

14. The method of claim 1, wherein said N-terminal cysteine is exposed by protein cleavage.

15. The method of claim 1, wherein said α-helical tetracysteine motif comprises [c]Cys-[c]Cys-X-X-[c]Cys-[c]Cys (SEQ ID NO:6), wherein X is any amino acid.

16. A 5'-nucleic acid-protein conjugate produced by the method of claim 1.

17. A 5'-nucleic acid-protein conjugate comprising:
(a) a nucleic acid covalently bound through a reactive group at its 5'-terminus to an N-terminus of a non-derivatized protein, wherein said protein comprises an N-terminal cysteine and said reactive group is an aminothiol reacting group; or
(b) a nucleic acid covalently bound through a 5'-terminal reactive group to an N-terminus of a non-derivatized protein, wherein said protein comprises an α-helical tetracysteine motif located proximal to the N-terminus and said reactive group is a bisarsenical group that is reactive with the tetracysteine group.

18. The conjugate of claim 17, wherein said conjugate is immobilized on a solid support.

19. The conjugate of claim 18, wherein said solid support is a bead or chip.

20. The conjugate of claim 18, wherein said conjugate is one of an array immobilized on said solid support.

21. The conjugate of claim 17, wherein said nucleic acid is about 20 nucleotides or greater in length.

22. The conjugate of claim 17, wherein said protein is about 20 amino acids or greater in length.

23. The conjugate of claim 17, wherein said nucleic acid is DNA.

24. The conjugate of claim 17, wherein said nucleic acid is RNA.

25. The conjugate of claim 17, wherein said nucleic acid comprises the coding sequence for said protein.

26. The conjugate of claim 17, wherein said α-helical tetracysteine motif comprises [c]Cys-[c]Cys-X-X-[c]Cys-[c]Cys (SEQ ID NO:6), wherein X is any amino acid.

* * * * *

SEQUENCE LISTING

```
<160> NUMBER OF SEQ ID NOS: 6

<210> SEQ ID NO 1
<211> LENGTH: 99
<212> TYPE: RNA
<213> ORGANISM: Artificial Sequence
<220> FEATURE:
<221> NAME/KEY: misc_feature
<222> LOCATION: 4-84
<223> OTHER INFORMATION: n = A,T,C or G
<223> OTHER INFORMATION: Thioester RNA

<400> SEQUENCE: 1
gggnnnnnnn nnnnnnnnnn nnnnnnnnnn nnnnnnnnnn nnnnnnnnnn nnnnnnnnnn      60
nnnnnnnnnn nnnnnnnnnn nnnccgugaa gagcauugg                             99

<210> SEQ ID NO 2
<211> LENGTH: 13
<212> TYPE: PRT
<213> ORGANISM: Artificial Sequence
<220> FEATURE:
<223> OTHER INFORMATION: Peptide 1

<400> SEQUENCE: 2

Cys Ser Lys Gly Phe Gly Phe Val Ser Phe Ser Tyr Lys
 1               5                   10
```

```
<210> SEQ ID NO 3
<211> LENGTH: 26
<212> TYPE: PRT
<213> ORGANISM: Artificial Sequence
<220> FEATURE:
<223> OTHER INFORMATION: Peptide 2

<400> SEQUENCE: 3

Cys Arg Lys Lys Arg Arg Gln Arg Arg Arg Pro Pro Gln Gly Ser Gln
1               5                   10                  15

Thr His Gln Val Ser Leu Ser Lys Gln Lys
            20                  25

<210> SEQ ID NO 4
<211> LENGTH: 13
<212> TYPE: PRT
<213> ORGANISM: Artificial Sequence
<220> FEATURE:
<223> OTHER INFORMATION: Peptide 3

<400> SEQUENCE: 4

Met Ser Lys Gly Phe Gly Phe Val Ser Phe Ser Tyr Lys
1               5                   10

<210> SEQ ID NO 5
<211> LENGTH: 11
<212> TYPE: PRT
<213> ORGANISM: Artificial Sequence
<220> FEATURE:
<221> NAME/KEY: VARIANT
<222> LOCATION: 4-11
<223> OTHER INFORMATION: Xaa = Any Amino Acid
<223> OTHER INFORMATION: Al pha-Helical Peptide

<400> SEQUENCE: 5

Ser Gly Gly Xaa Xaa Xaa Xaa Xaa Xaa Xaa Xaa
1               5                   10

<210> SEQ ID NO 6
<211> LENGTH: 6
<212> TYPE: PRT
<213> ORGANISM: Artificial Sequence
<220> FEATURE:
<221> NAME/KEY: VARIANT
<222> LOCATION: 3,4
<223> OTHER INFORMATION: Xaa = any amino acid
<223> OTHER INFORMATION: Tetracysteine motif

<400> SEQUENCE: 6

Cys Cys Xaa Xaa Cys Cys
1               5
```